(12) United States Patent
Mays

(10) Patent No.: US 6,520,774 B1
(45) Date of Patent: Feb. 18, 2003

(54) HIGHLY FLEXIBLE INSTRUMENT FOR MEDICAL APPLICATIONS

(75) Inventor: Ralph C. Mays, Tulsa, OK (US)

(73) Assignee: Pro Post, Inc., Tulsa, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/811,981

(22) Filed: Mar. 19, 2001

Related U.S. Application Data

(63) Continuation of application No. 09/469,553, filed on Dec. 22, 1999, now Pat. No. 6,267,592.

(51) Int. Cl.$^7$ ................................. A61C 5/02
(52) U.S. Cl. .................. 433/102; 433/224; 606/170
(58) Field of Search ................................. 433/102, 165, 433/166, 224; 30/116, 117, 352; 83/651.1; 15/104.068, 104.069; 606/167, 170, 180, 183

(56) References Cited

U.S. PATENT DOCUMENTS

| | | | |
|---|---|---|---|
| 184,804 A | * | 11/1876 | Stohlmann |
| 318,173 A | * | 5/1885 | Donaldson |
| 966,100 A | * | 8/1910 | Johnson |
| 1,147,824 A | * | 7/1915 | Soule |
| 1,307,017 A | * | 6/1919 | Movshovitch |
| 1,811,205 A | * | 6/1931 | Lee |
| 2,304,281 A | * | 12/1942 | Riley |
| 2,604,883 A | * | 7/1952 | D'Avaucourt |
| 2,774,400 A | * | 12/1956 | Frickhofen |
| 3,828,790 A | * | 8/1974 | Curtiss et al. |
| 4,260,379 A | * | 4/1981 | Groves et al. ............... 433/102 |
| 4,706,671 A | * | 11/1987 | Weinrib |
| 4,828,420 A | * | 5/1989 | Orsuka et al. ............... 401/268 |
| 4,934,934 A | | 6/1990 | Arpaio, Jr. et al. ......... 433/102 |
| 5,075,062 A | * | 12/1991 | Karpiel |
| 5,106,298 A | | 4/1992 | Heath et al. ................. 433/102 |
| 5,334,211 A | * | 8/1994 | Shiber ......................... 606/159 |
| 5,339,480 A | * | 8/1994 | Murg et al. .................... 15/106 |
| 5,344,315 A | * | 9/1994 | Hanson ......................... 433/20 |
| 5,380,200 A | * | 1/1995 | Heath et al. ................. 433/102 |
| 5,628,674 A | | 5/1997 | Heath et al. .................... 451/48 |
| 5,722,423 A | * | 3/1998 | Lind et al. |
| 5,775,902 A | * | 7/1998 | Matsutami et al. ......... 433/102 |
| 6,267,592 B1 | * | 7/2001 | Mays ........................... 433/102 |

* cited by examiner

Primary Examiner—Ralph A. Lewis
(74) Attorney, Agent, or Firm—Gable & Gotwals; Paul H. Johnson

(57) ABSTRACT

A highly flexible instrument particularly useful in medical applications is elongated and formed of a plurality of flexible metallic strands, at least one strand being spirally wound and having a scraping edge thereon.

26 Claims, 4 Drawing Sheets

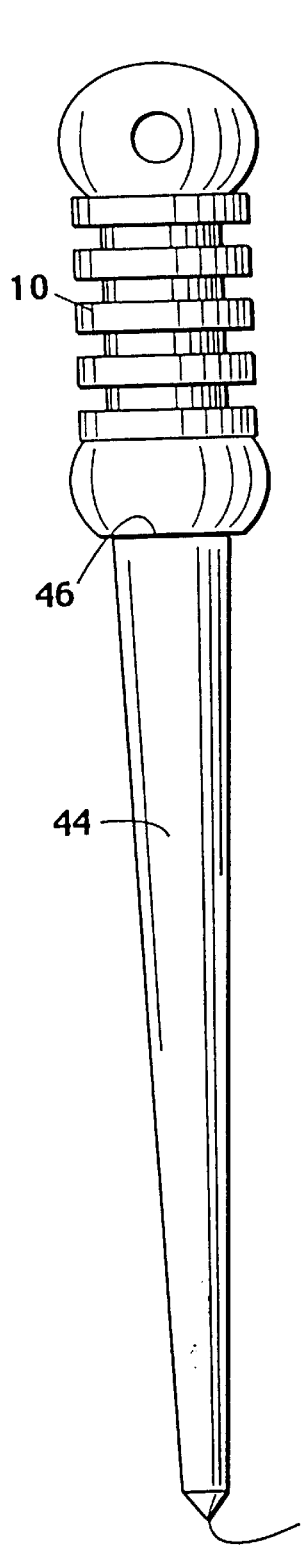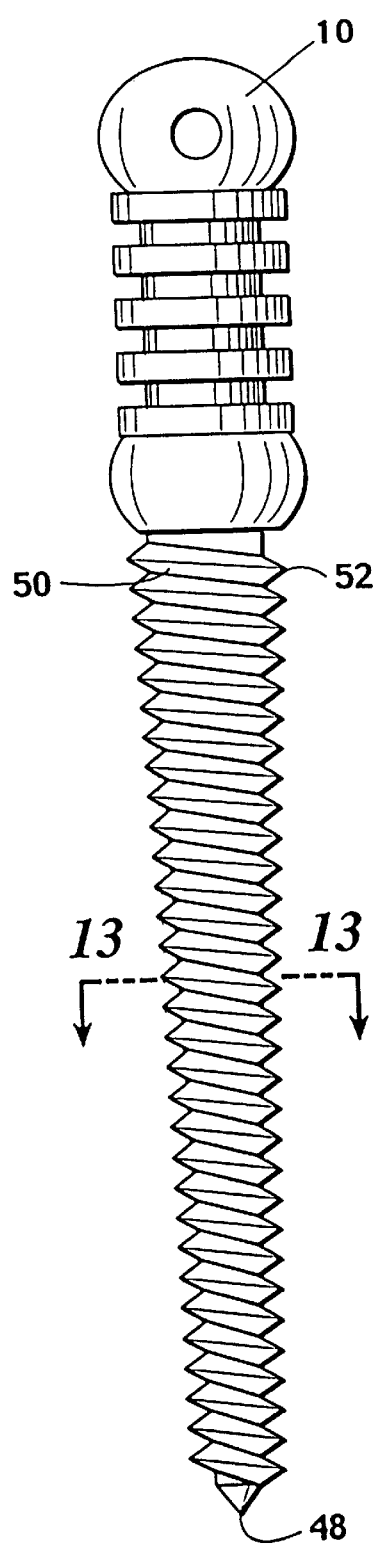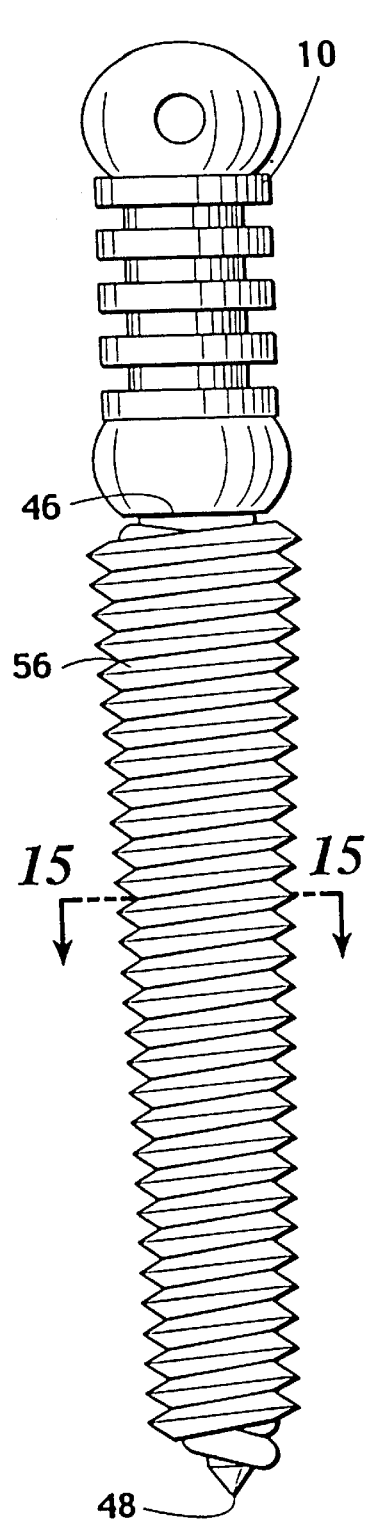
*Fig. 11*  *Fig. 12*  *Fig. 14*

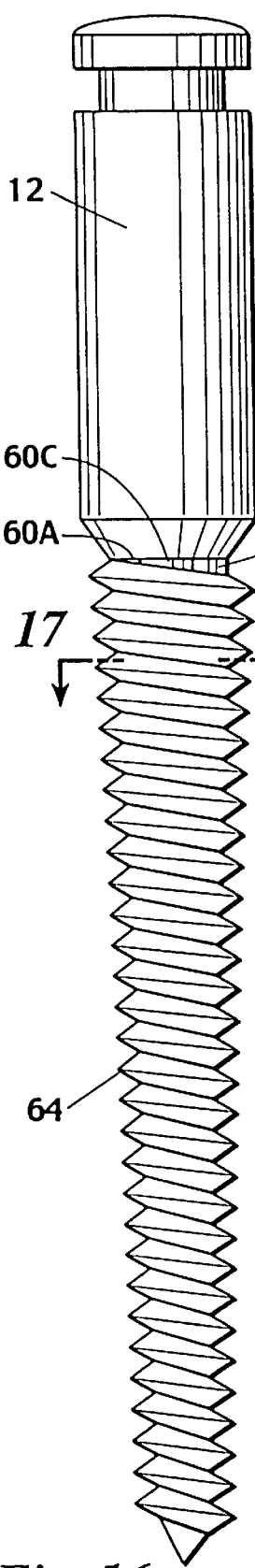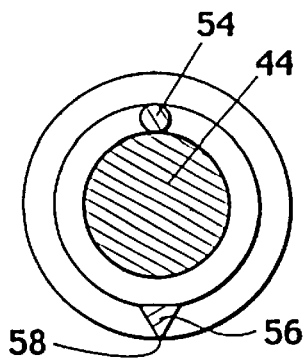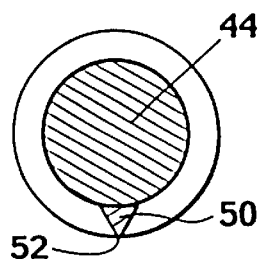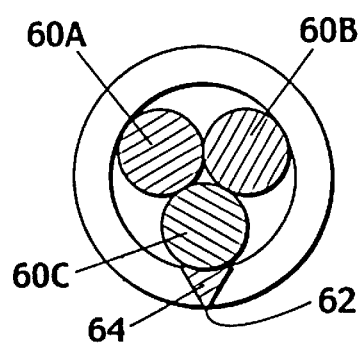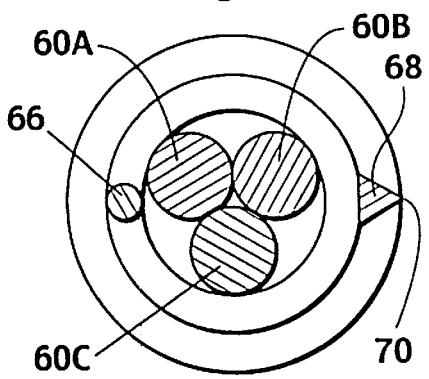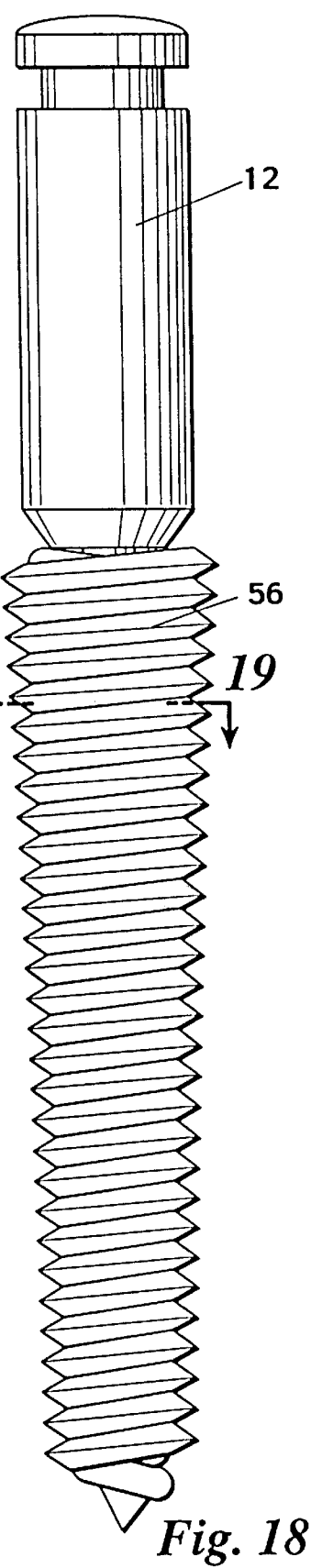
Fig. 15
Fig. 13
Fig. 17
Fig. 19
Fig. 16
Fig. 18

HIGHLY FLEXIBLE INSTRUMENT FOR MEDICAL APPLICATIONS

CROSS-REFERENCE

This is a continuation application of U.S. application Ser. No. 09/469,553, now U.S. Pat. No. 6,267,592 entitled, A HIGHLY FLEXIBLE INSTRUMENT FOR MEDICAL AND/OR DENTAL APPLICATIONS filed Dec. 22, 1999.

BACKGROUND OF THE INVENTION

1. Field of the Invention

This invention relates to a highly flexible instrument that is particularly adaptable for use as an endodontic instrument, most particularly, an endodontic file for use by practitioners in removing the pulpal material from an exposed root of a tooth and for shaping the root canal to receive filler material, usually gutta-percha. One of the most significant advancements in dentistry in recent years has been improved treatment of abscessed teeth. In the past a tooth, once abscessed, was usually pulled as the only remedy for removing the intense pain usually created when a tooth is abscessed. By "abscessed" usually means that the root canal of the tooth becomes infected and the infection causes pressure on the tooth and the nerve endings associated therewith that result in sometimes almost unbearable pain. With the advent of endodontics the drastic measure of extracting a tooth that has become abscessed has been eliminated.

The first step in the endodontic treatment of an abscessed tooth is to drill an opening in the crown of the tooth to provide access to the root canal. Once the root canal adjacent the crown is exposed, the practitioner then must thoroughly clean the root canal of pulpal material since if the pulpal material is not thoroughly and carefully removed it can be the source of continued infection within the interior of the tooth. Not only is it necessary that the pulpal material be clean but the root canal usually must be shaped in such a way as to permit careful filling of the root canal with a filler material. While other types of filler materials have been provided still at the present time the most common filler is a paste-like material referred to as "gutta-percha." If the canal is not properly cleaned and shaped the step of filling with gutta-percha may leave void areas that invite the introduction into the root canal of organic matter that can be followed by bacterial action. For these reasons much of the effort by a practitioner to successfully accomplish the endodontic treatment of an abscessed tooth is the cleaning and shaping of the root canal and these steps are accomplished utilizing small diameter tapered files that are inserted by the practitioner through the exposed crown area into the root canal. The canal must be cleaned from the crownal area advancing to the root apex. Root canals naturally occur in a tapered configuration, that is the cross-sectional diameter of the root canal is usually greater near the crown of the tooth and usually is at a minimum at the apex of the tooth, that is the distal end of the root of the tooth. While the root canal is naturally tapered it is not tapered symmetrically and the canal can have inclusions in intermediate portions between the apex and the crown area that interfere with the passage of filler material. Therefore the crown must be shaped to remove unnecessary intrusions into the canal and to improve the chances that the practitioner can successfully fill the root canal with filler material.

Files are usually provided with a small cylindrical plastic handle portion by which the practitioner manually manipulates the files. By "manipulation" means inserting a file into a canal and reciprocating it to file away intrusions and at the same time to gather pulpal material and the results of the scraping action. Typically the practitioner inserts a file to the point of resistance and then rotates and reciprocates the file to engage spiral scraping edges with the canal wall and then extract the file to remove pulpal material and matter scraped from the wall. This procedure is repeated as necessary to clean the entire length of the canal. In the cleaning process the practitioner usually starts with a file of a small diameter and then, as progress is made in cleaning the canal, larger diameter files are employed until the root canal is shaped and cleaned to the apex. Accordingly, endodontic files usually come in sets of standard tapers and varying from small to larger diameters.

Root canals are characteristically not straight. Some root canals curve more than others but few are perfectly straight from the crown to the apex. Therefore it is important that files be flexible so as to be able to follow the natural curvature of the root canal as it is cleaned and shaped from the tooth crown to the tooth apex. If a file is too stiff it can result in the file protruding through a side wall of the root which can introduce an area of infection into the tooth and therefore is highly undesirable. Further, if the file is stiff it is less successful in cleaning the entire area of a canal since the stiffness will cause the file to be deflected drastically to one side of a curve in a canal leaving a portion of the wall that defines the inside of the curve unexposed to the action of the file for cleaning and shaping. Therefore, a high degree of flexibility is a very desirable characteristic of an endodontic file.

In addition, the strength of a file is very important. In the process of reciprocating and rotating a file in a tooth it is possible for the file to break off leaving a broken part in the tooth. This creates a serious problem for the practitioner. Accordingly, it has long been a desire of the dental profession to have available dental files that are highly flexible and yet strong to resist separation as a result of a torsional twist or pulling action as a file is manipulated within a root canal. The present invention provides a way of substantially increasing the flexibility of dental files while at the same time increasing resistance against torsional or elongational separation.

2. Prior Art

For additional background information on the construction and use of highly flexible instruments, such as endodontic files, reference can be had to the following previously issued United States patents including the references cited in each of them.

| U.S. PAT. NO. | INVENTOR | TITLE |
| --- | --- | --- |
| 4,934,934 | Arpaio, Jr. et al. | Dental File/Reamer Instrument |
| 5,106,298 | Heath et al. | Endodontic Dental Instrument |
| 5,628,674 | Heath et al. | Endodontic Instrument |

SUMMARY OF THE INVENTION

A highly flexible instrument for medical and/or dental applications has an elongated metallic body formed of a plurality of flexible metallic strands. One application of the invention is an endodontic file in which the instrument has a scraping edge thereon. The scraping edge can be formed by employing at least one metallic strand that is non-circular in configuration, such as triangular. A spiraled scraping edge is preferably achieved by winding a non-circular cross-sectional strand on the outer surface of a plurality of base strands. The invention can be practiced by employing one or more central strands, surrounded by a spirally wound strand that is non-circular in cross-section providing a spiraled scraping edge. Another embodiment employs one or more central strands surrounding by a first spirally wound strand and on top of it a second strand spirally wound in the opposite direction. The outermost spiraled strand is non-circular to provide a scraping edge.

A better and more complete understanding of the invention will be obtained from the following description of the preferred embodiments having reference to the attached drawings.

BRIEF DESCRIPTION OF THE DRAWINGS

FIG. 1 is pentagonal as an illustration of one non-circular cross-sectional embodiment.

FIG. 11 is an elevational view of the first stage of manufacturing a multi-strand endodontic file showing a single base strand and a handle for manual manipulation.

FIG. 12 is an elevational view of a file employing the apparatus of FIG. 11 in which an elongated strand is wound on the center strand and in which the elongated strand is of triangular cross-section. The embodiment illustrated in FIGS. 11 and 12 provides a tapered file in which the outer spirally wound strand is not required to be tapered and provides a file that does not require machining after assembly.

FIG. 13 is a cross-sectional view taken along the line 13—13 of FIG. 12.

FIG. 14 is an elevational view of a file in which a tapered center strand that is circular in cross-section is wound first in one spiral direction with a smaller diameter strand that is non-tapered and is circular in cross-section followed by a spirally wound strand on the outer surface that is triangular in cross-section.

FIG. 15 is a cross-sectional view taken along line 15—15 of FIG. 14.

FIG. 16 shows a file having a handle portion configured to be received in a hand piece by which the file can be rotated. The file of FIG. 12 includes three central elongated tapered strands surrounded by a single spiral wound strand having a triangular cross-sectional shape to form scraping edges on the exterior surface.

FIG. 17 is a cross-sectional view taken along line 17—17 of FIG. 16 showing three central strands that are tapered and are of circular cross-sectional configuration surrounded by a single strand that is spirally wound on the three circular strands, the spiraled wound strand being triangular in cross-section.

FIG. 18 is an alternate embodiment of a file of FIG. 16 having multiple central strands that are circular in cross-section surrounded by a first spiral wound layer that is also circular in cross-section followed by an outer spiraled wound strand that is triangular in cross-section. The outer spiral wound strand is wound in a direction opposite to the inner spiral wound layer.

FIG. 19 is a cross-sectional view taken along the line 19—19 of FIG. 3.

DETAILED DESCRIPTION OF THE PREFERRED EMBODIMENTS

The invention described herein is a highly flexible instrument for medical and/or dental applications. One specific application of the invention is as a highly flexible file useful in removing plaque from veins and arteries and is particularly useful for removing pulpal material from root canals. Such files are called "endodontic files" and the invention will be described as it is used in endodontic file applications, however, this is not to be taken as a limitation on the application of the invention.

Endodontic files are used in two basic ways. In the most common way the file has at its proximal end a small cylindrical handle, usually made of plastic that is manipulated between the thumb and forefinger of the practitioner. A practitioner inserts the file into a root canal and manually reciprocates and rotates it to clean and shape the canal. The other basic type of endodontic file is used in a hand piece—that is, a handheld instrument that provides rotation like a drill. The file head portion is inserted into a chuck device in the hand piece and the practitioner can control the rotation thereof as the file is moved into and out of a root canal. FIGS. 11 through 14 show examples of files of the first type, that is wherein each file has a handle portion 10 for manual manipulation. FIGS. 16 and 19 are external views of files in which the handle portion 12 is configured to be received in the chuck of a handpiece by which the file can be rotated as used by a practitioner.

Normally files come in sets of different diameters. A practitioner normally starts with a small diameter and as the root canal is cleaned and shaped switches gradually to larger diameters until the root canal is cleaned and shaped from the crown area down to the root apex and is in condition for receiving the application of filler material, such as gutta-percha. This invention provides an endodontic file that functions in the same way and for the same purpose as endodontic files in present use but provides a file that has improved flexibility and resistance against breakage. Essentially, improved flexibility is achieved by employing the concept of utilizing a plurality of flexible metal strands that form the file body. This contrasts with files as used today wherein the file body is a unitary metallic member usually basically cylindrical on its working surface and tapered from a proximal end to the distal end with one or more spiral grooves providing spiral lands with scraping edges that serve to scrape a root canal as the file is used.

Figures 1, 2, 3:
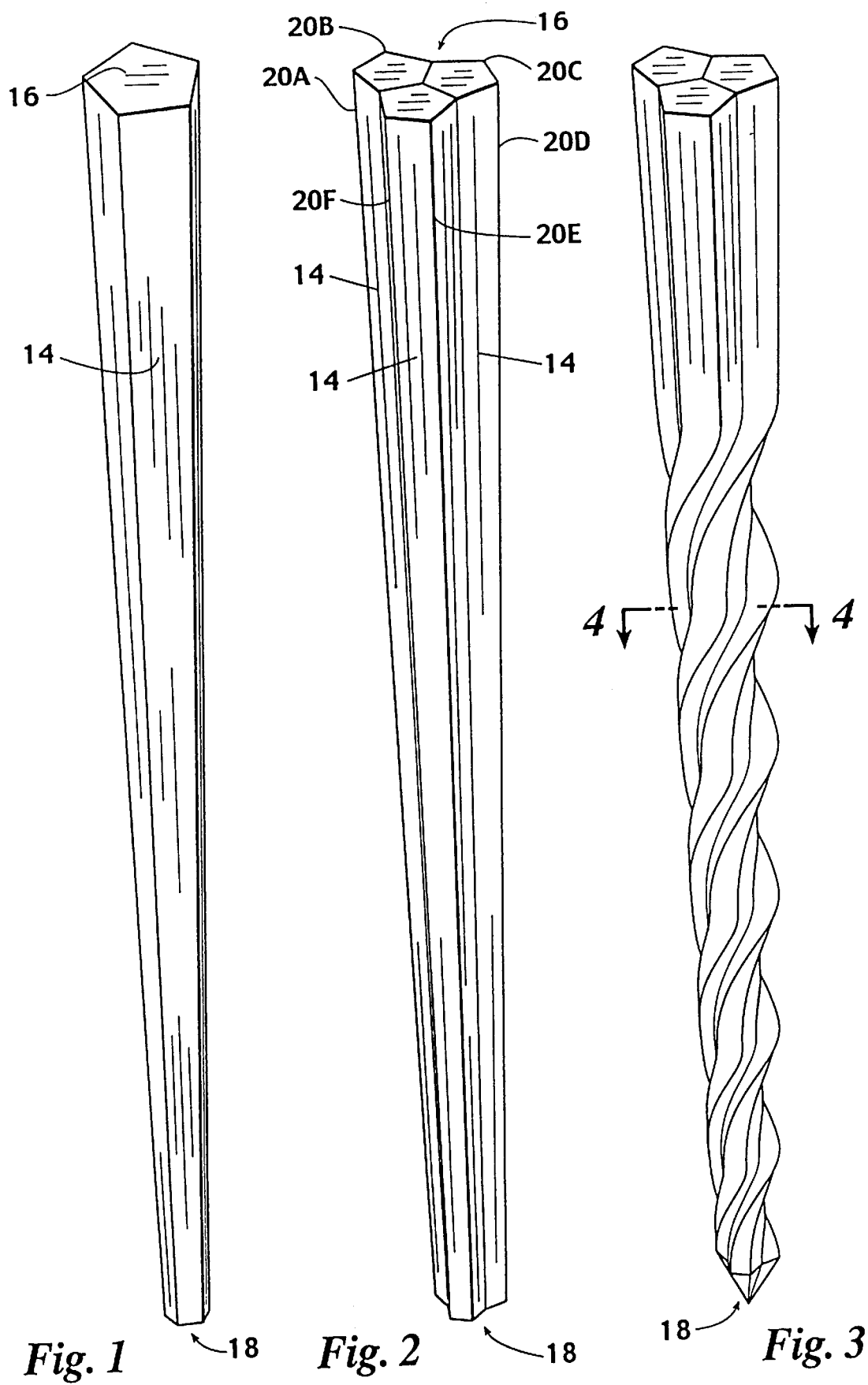
FIG. 1 is an elevational isometric view, highly enlarged, of an elongated metal strand that is tapered from a proximal end towards a distal end and is non-circular in cross-section.
FIG. 2 is an isometric elevational view of three of the strands of FIG. 1 assembled together.
FIG. 3 is a view of the three strands of FIG. 2 wherein the working portion of the file has been twisted to form a spiral external configuration that provides three interleaved spiral scraping edges.

FIG. 1 shows an example of a single flexible metallic strand 14 that can be employed in the manufacture of an endodontic file. Strand 14 has a proximal end 16 and a distal end 18 and is non-circular in cross-section. From the isometric external view of FIG. 1 it can be seen that any cross-section taken perpendicular the length of strand 14 is pentagonal. This is by way of example only. In practicing the invention the file body or working portion is preferably formed of a plurality of elongated metal strands and in one embodiment of the invention the metal strands are non-circular in cross-section. FIG. 1 is an example of one type of non-circular strand.

Figure 4:
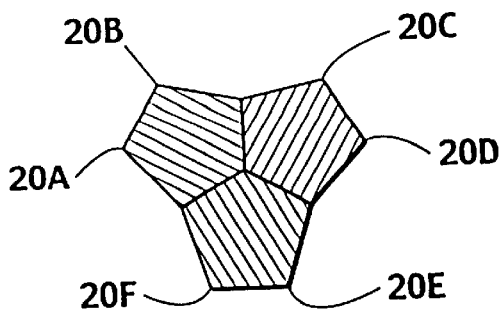
FIG. 4 is a cross-sectional view of one configuration of a file body formed of three pentagonal strands as taken along the line 4—4 of FIG. 3.

FIG. 2 is a diagrammatic view of an assembly of three elongated flexible metallic pentagonal strands 14 assembled together to form a first phase in the manufacture of the body of an endodontic file. FIG. 3 shows the assembly of FIG. 2 in which the working portion has been twisted providing a plurality of spiral scraping edges. It can be seen in FIG. 4 that the assembly of three pentagonal members provides six longitudinal edges indicated by 20A through 20F. When the working portion of the file body is twisted as in FIG. 3 all of the edges 20A through 20F take a spiral pattern and provide interleaved spiral scraping edges. The file distal end 18 of the assembly is tapered or pointed so that the file will be guided as it follows a root canal of a tooth during an endodontic procedure.

The use of elongated strands having a pentagonal cross-section as shown in FIGS. 1 through 4 is exemplary of the concept of manufacturing endodontic files out of a plurality of strands in which the strands are non-circular in cross-section so that when the multiple strands are assembled and twisted spiral scraping edges are provided without the requirement of machining the exterior surface of the file. If desirable, machining can be applied to the spiral wound assembly of FIG. 3 to reshape the scraping edges.

Figure 5:
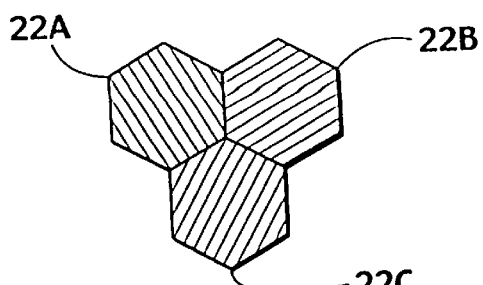
FIG. 5 is a cross-sectional view of an alternate embodiment showing three strands each having a hexagonal shape.

FIG. 5 is a cross-sectional view of an assembly of three elongated strands wherein each of the strands has a hexagonal configuration. This configuration provides, after the assembly is twisted as in FIG. 3, three scraping edges 22A, 22B and 22C showing that the number of scraping edges varies according to the nature of the assembly.

Figure 6:
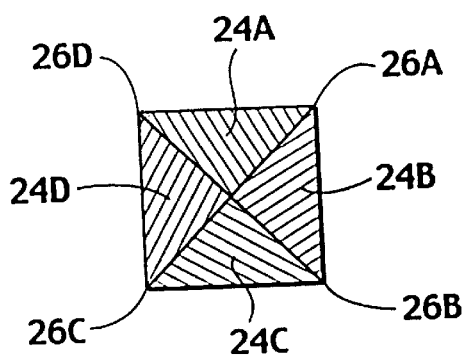
FIG. 6 shows in cross-section four strands each having a triangular configuration fitted together to form a square.

FIGS. 6 through 10 show additional cross-sectional embodiments wherein the file body portion is formed of a plurality of strands of different cross-sectional configurations. For instance, FIG. 6 is a cross-section of an assembly of strands used in manufacturing an endodontic file employing four elongated strands 24A through 24D when the assembly of FIG. 6 is twisted four interleaved spiraled scraping edges 26A through 26D are formed.

Figure 7:
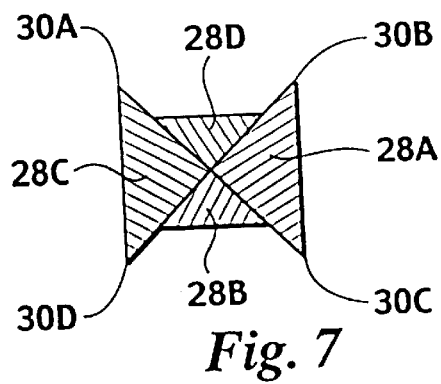
FIG. 7 is an alternate embodiment of FIG. 6 showing a cross-sectional view of four strands, each of triangular cross-sectional configuration, but wherein the strands are of different sizes.

FIG. 7 shows a different embodiment in cross-section in which four triangular strands are employed, that is 28A through 28D but in which the strands have two different cross-sectional shapes. Strands 28A and 28C have triangular cross-sections equally dimensioned, that is geometrically the same, while strands 28B and 28D are triangular but of reduced dimensions. The assembly of FIG. 7 when twisted will provide an elongated shaft having four scraping edges 30A through 30D. The configuration of FIG. 7 is considered superior to that of FIG. 6 since in FIG. 7 the scraping edges 30A are formed at intersecting sides of the same strand in each case instead of as in FIG. 6 wherein scraping edges 26A–26D are formed at the intersection of two strands. Further, scraping edges 30A–30D of FIG. 7 are defined by acute angles whereas in FIG. 6 the scraping edges 26A–26D are defined by right angles.

Figure 8:
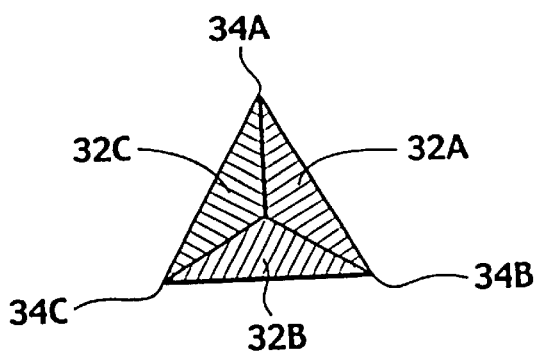
FIG. 8 is a cross-sectional view showing three triangular strands together to form a file body wherein the overall body is triangular providing three scraping edges.

The cross-sectional view of FIG. 8 shows the use of three triangular cross-sectioned strands 32A–32C that provide three edges 34A–34C.

Figure 9:
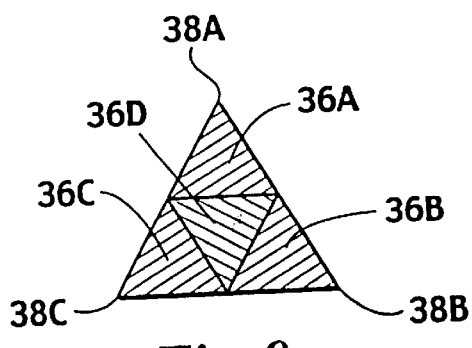
FIG. 9 shows four strands, each of triangular configuration, assembled so that the cross-section of the file body is triangular providing three scraping edges.

FIG. 9 is a cross-sectional view of another assembly of elongated strands of non-circular cross-section providing an overall triangular cross-sectional arrangement wherein four strands 36A–36D are employed. Each of the strands is of the same cross-sectional triangular shape assembled in a way so that the four strands provide three scraping edges 38A–38C. When the assembly of FIG. 9 is twisted it provides a file shaft portion having three spirally wound scraping edges 38A–38C and wherein each of the spiral edges is at an acute angle and each edge is formed integrally of the same strand. The arrangement of FIG. 9 is superior to that of FIG. 8 for the same reason as explained in the comparison of FIGS. 6 and 7—that is, in FIG. 9 the cutting edges 38A–38C are integrally formed each by a single strand.

Figure 10:
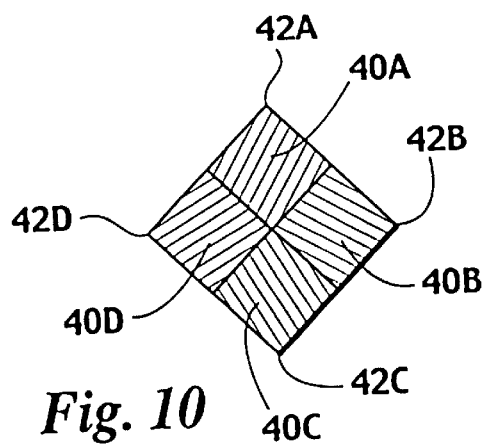
FIG. 10 shows the arrangement wherein four strands having square cross-sections are assembled together to form a file body that is square in cross-section.

FIG. 10 is a cross-sectional view of four strands 40A–40D, each strand being of the same square cross-sectional shape. This assembly provides four scraping edges 42A–42D when the assembly is twisted as in FIG. 3.

The examples of FIGS. 1 through 10 are illustrative of various ways in which the invention may be practiced wherein an endodontic file has a shaft formed of a plurality of elongated flexible tapered strands that are spirally wound about each other to provide spiral scraping edges.

To prevent the plurality of tapered flexible metallic strands from separating from each other after being assembled together the distal end portion 18 as indicated in FIG. 3 can be treated to bond the strands together. This can be achieved by subjecting tip 18 to a fusing temperature or solder may be applied to the tip end portion. Alternatively, a high strength epoxy may be employed to bond the strands to each other at the tip 18.

Whereas known endodontic files in use today employ a solid unitary elongated tapered metal shaft from the proximal to the distal portion the endodontic file of this invention is different in that it employs a plurality of tapered flexible metallic strands to form the shaft of an endodontic file. There are two significant advantages achieved by the use of a plurality of strands versus forming a file wherein the shaft is unitary. First, a plurality of strands provides significantly increased flexibility compared to a single integral shaft body. The advantages of flexibility are easy to understand when the flexibility of multi-strand copper wire is compared with a single solid copper wire having the same current carrying capacity. The root canals of human teeth are typically not straight but are invariably curved as the canal extends from the root apex to adjacent the tooth crown. For this reason it is important that endodontic files be flexible so as to follow the contour of a canal as a file is inserted into the canal.

In addition to flexibility it is also important that endodontic files be resistant to breakage, that is resistant to being severed by elongational pull or torsional twists. If a lower portion of a file breaks off in a root canal it is considered a serious problem by endodontists and therefore every effort is made to prevent breakage of a file in the process of cleaning and shaping a root canal. Thus, the designers of endodontic files are forced into compromising between strength and flexibility. Endodontic files are customarily made of steel, usually stainless steel. Stainless steel is in many ways an ideal metal for making a file since it is typically relatively strong compared to other metals is relatively flexible and chemically resists reaction with the pulpal material in a tooth. However, recent tests have indicated that certain metal alloys improved flexibility without significant loss of elongation or torsional strength. A most prominent alloy having such improved flexibility is a combination of nickel and titanium and is referred to in the trade as "Nitinol." Comparisons made of the relative advantages of stainless steel and Nitinol were published in an article entitled "An Initial Investigation of the Bending and the Torsional Properties of Nitinol Root Canal Files", *Journal of Endodontics*, Vol. 14, No. 7, July, 1988 at pages 346–351. The advantages of the endodontic file of this invention that improve flexibility by the use of a plurality of metal strands are enhanced when the metal strands are formed of a high flexibility, high strength alloy such as nickel-titanium or Nitinol. Nitinol typically consists of about 40% titanium and 60% nickel although the exact percentages of the alloy can vary. One disadvantage in the use of nickel-titanium appears that the process of grinding cutting surfaces on a tapered shaft made of Nitinol frequently results in the cutting surfaces having ragged edges such as caused by metal deposits as a result of the grinding operation. In the invention herein where a plurality of flexible tapered metal strands of non-cross-sectional configuration are employed, the scraping edges are formed without the necessity of further machining after the file is formed thus eliminating a problem which has existed in some types of previously known endodontic files manufactured with nickel-titanium shafts.

FIGS. 11 through 15 show alternate embodiments of the invention. The first embodiment is shown in FIGS. 11, 12 and 13. FIG. 11 shows an elongated unitary metallic shaft 44 that is tapered from a proximal end 46 to a pointed distal end 48. The upper portion of the proximal end 46 of shaft 44 is encompassed within a plastic formed handle portion 10 as previously described. The shaft 44 of FIG. 13 is round in cross-section however it could be of other cross-sectional arrangements.

Spirally wrapped about shaft 44 is a metallic strand 50 having a non-circular cross section, in this case a triangular cross-section as seen in FIG. 12. The spirally wound strand provides a spiral scraping edge 52 that extends from the shaft proximal portion 46 to distal end 48. It should be noted in comparing FIGS. 11, 12 and 13 that the base shaft 44 is tapered in the way that endodontic files are typically tapered however the spiral wound strand 50 does not have to be tapered. This is one embodiment by which the invention of FIGS. 11, 12 and 13 may be practiced. Spirally wound strand 50 could be tapered, having a smaller cross-sectional size as the strand approaches file distal end 48 (not shown).

FIG. 11 and the cross-sectional view of FIG. 15 show shaft 44 as being of circular cross section and unitary that is, a single base shaft extends from the distal to the proximal end. It is understood that instead of a unitary shaft 44, a tapered central shaft can be formed using a plurality of individual tapered strands such as the tapered strands of FIG. 2 wherein the strands can have a variety of cross-sectional configurations.

The advantage of the endodontic file of FIGS. 11 through 13 is that the central shaft 44, whether unitary or made up of a plurality of tapered strands, can be of a relatively smaller diameter since the ultimate operating diameter of the file is achieved by spirally wound strand 50, thus providing a file shaft body of smaller cross-sectional area and therefore greater flexibility. Further, the spirally wound strand 50 provides a cutting edge and adds torsional strength without significantly adding to the rigidity of the file. Thus the advantages of the embodiment of FIGS. 11 through 13 are increased flexibility and in addition, the provision of a file having a spiraled scraping edge wherein no machining work is required to be done on the assembled file shaft.

The end of spirally wound strand 50 at distal end 48 is preferably secured to the shaft such as by spot welding, solder, epoxy bonding or otherwise and the same is true at the upper end of the spirally wound strand 50 at the base shaft proximal end 46. In addition, the spirally wound strand 50 can be attached at other places along the length of shaft 44 such as by the use of laser welding as a way of ensuring a secure relationship between inner shaft 44 and spirally wound shaft 50 without significantly detracting from the high flexibility of the total assembly.

FIGS. 14 and 15 show an alternate embodiment employing the basic substructure of the file as shown in FIGS. 11 through 13, that is a file with an elongated shaft 44 that may be unitary as illustrated. In the embodiment of FIGS. 14 and 15 the elongated tapered central shaft 44 has a first spirally wound small diameter strand 54 that, as shown in FIG. 15, may be circular in cross-section. The small diameter strand 54 is wound helically on shaft 44 from the proximal end 14 adjacent handle 10 down to adjacent the distal end 44. A second outer spiraled strand 56 is then helically wound on top of the inner spirally wound strand 54. The outer spiraled strand 56 is preferably wound in the opposite direction of the inner spirally wound strand 54. The end portions of inner spirally wound strand 54 are secured to base shaft 54 at the opposite ends thereof such as by welding, soldering, braising, adhesive, etc. In like manner the outer spirally wound strand 56 is secured to the assembly by welding, soldering, braising, adhesive, etc. The second small size outer spiraled strand 56 is non-circular in cross-section, such as triangular as shown in FIGS. 14 and 15 to provide a spiraled scraping edge 58.

The advantages of the arrangement of FIGS. 14 and 16 having a double spiral wrapping around the base shaft as compared to the single spiraled wrapping of FIGS. 12 and 13 is that in the embodiment of FIGS. 14 and 16 the resistance to torsional separation of the file is substantially increased. This is so since rotation of the shaft proximal end relative to the distal end in either clockwise or counter-clockwise direction will result in applying tension to either the inner spirally wound strand 54 or the outer spirally wound strand 56. Therefore, the embodiment of FIGS. 14 and 15 achieve an endodontic file having a high degree of flexibility and resistance to torsional separation and the scraping edge does not need to be machined on to the file body as with existing types of files.

FIGS. 16 and 17 show an embodiment that is like FIGS. 12 and 13 with only two changes. In FIGS. 16 and 17 handle 12 is configured to be received in a handpiece as has been previously described. Further, the central shaft of the file of FIGS. 16 and 17 is formed of a plurality of elongated tapered shaft portions 60A–60C. The use of three strands to form the central shaft of the file is only exemplary as the shaft can be made with any number of strands. In the arrangement of FIGS. 16 and 17 the tapered central strands 60A and 60C may be straight, that is they need not necessarily be twisted around each other although this could be done. Further, the central strands 60A–60C are shown to be circular in cross-section although they could be of other cross-sectional configurations.

Wrapped around the plurality of central tapered strands 60A–60C is a spirally wound strand 62 that, in the illustrated arrangement, is of uniform dimension from end to end although, as previously explained, it could be tapered. Economy of manufacture obviously suggests the use of a non-tapered strand 62. The strand is non-circular cross-sectional configuration such as a triangle as illustrated in FIG. 17 providing a spiral scraping edge 64.

The final illustrated embodiment is shown in FIGS. 18 and 19 and is different from the embodiment of FIGS. 14 and 15 in two ways, that is by the use of a handle portion 12 intended for insertion into a dental handpiece and wherein the central shaft is formed of a plurality of elongated tapered metallic strands 60A–60C as has been described with reference to FIGS. 16 and 17. Wrapped around the elongated tapered central strand 60A–60C is a first spirally wound small diameter inner strand 66 which, as was explained with reference to FIG. 15, may be either circular or non-circular in cross-sectional configuration. Spirally wound inner strand 66 may be of uniform external diameter although optionally it could be of tapered diameter.

Helically wound on the exterior of inner strand 66 is outer strand 68, the outer strand being wound in an opposite helically direction from inner strand 60. The strands are secured at their ends to the central shaft strand 60A–60C and at spaced apart intermediate points if desired. Outer strand 68, when triangular in cross-section as shown, provides a spiral scraping edge 70. The inner and outer spirals obtained by inner strand 66 and outer strand 68 have advantages as previously indicated, that is resistance to torsional breakage while at the same time maintaining high flexibility.

It needs to be pointed out that the drawings herein are not dimensionally representative of endodontic files but are illustrative of the principles by which flexible files of this invention may be manufactured. The typical endodontic file has a shaft that extends from a handle not more than approximately three centimeters and the typical endodontic file including the handle portion itself is typically approximately four centimeters in length. The sizes illustrated herein are grossly enlarged.

The embodiments of FIGS. 11 through 19 are particularly adaptable to the use of nickel-titanium alloy in their manufacture for the reasons previously described. Further, in the embodiments herein wherein a plurality of strands are employed the alloy of which the strands are made can be mixed, that is not all of the strands in any configuration need to be of the same alloy. As an example, in the embodiments of FIGS. 11 and 12 the main shaft 44 may be of nickel-titanium alloy whereas the spirally wound strands 50 in FIG. 12 or 54 and 56 of FIG. 14 may be stainless steel or some other alloy, the reason being that the small dimensions of the spirally wound strands lend themselves to inherently stiffer material without dramatically increasing the overall stiffness of the finished endodontic file.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein; the more specific meaning is meant.

Whereas, the present invention has been described in relation to the drawings attached hereto, it should be understood that other and further modifications, apart from those shown or suggested herein, may be made within the spirit and scope of this invention.

What is claimed is:

1. A highly flexible instrument for medical applications comprising;
   an elongated instrument body formed of a plurality of elongated flexible metallic strands including at least one central strand that is tapered in cross-section from a larger dimension adjacent said body proximal end to a smaller dimension adjacent said body distal end, said at least one central strand being surrounded by at least one spirally wound strand having at least a portion that is non-circular in cross-section.

2. An instrument according to claim 1 wherein said body has a proximal end and a distal end, and including a handle portion at said proximal end.

3. An instrument according to claim 2 wherein said handle portion is configured for engagement by a mechanically rotated chuck.

4. An instrument according to claim 2 wherein said handle portion is configured for manual manipulation.

5. An instrument according to claim 1 wherein at least some of said plurality of elongated flexible metallic strands are twisted about each other and wherein said scraping edge is formed by the cross-sectional shape of one of said metallic strands.

6. An instrument according to claim 1 wherein at least one of said strands has at least a portion that is at least substantially triangular in cross-section.

7. An instrument according to claim 1 wherein at least one of said strands has a portion that is pentagonal in cross-sections.

8. An instrument according to claim 1 wherein at least one of said strands has a portion that is hexagonal in cross-sections.

9. An instrument according to claim 1 wherein said strands are bonded to each other at a body distal end.

10. An instrument according to claim 1 wherein at least some of said strands are twisted about each other.

11. A highly flexible instrument for medical applications according to claim 1 wherein said at least one spirally wound strand that is non-circular in cross-section provides at least one scraping edge.

12. A highly flexible medical instrument having a free end comprising:
    an elongated tapered body having a proximal end and a reduced diameter distal end and formed of a plurality of elongated flexible metallic strands extending from adjacent said proximal end to adjacent said distal end, —one of said strands being a central strand tapered in cross-section from a larger dimension adjacent said proximal end to a smallest dimension adjacent said distal end surrounded by—at least one—spirally wound—strand having at least one scraping edge.

13. An instrument according to claim 12 wherein said body is uniformly tapered from said proximal end to said distal end.

14. An instrument according to claim 13 including a handle portion at said body proximal end.

15. An instrument according to claim 12 wherein said body has a handle portion at said proximal end.

16. An instrument according to claim 15 wherein said handle portion is configured for engagement by a mechanically rotated chuck.

17. An instrument according to claim 15 wherein said handle portion is configured for manual manipulation.

18. An instrument according to claim 12 wherein said scraping edge is spiraled.

19. An instrument according to claim 12 wherein at least some of said plurality of elongated flexible metallic strands are twisted about each other and wherein said scraping edge is formed by the cross-sectional shape of one of said metallic strands.

20. An instrument according to claim 12 wherein at least one of said strands has at least a portion that is at least substantially triangular in cross-section.

21. An instrument according to claim 12 wherein at least one of said strands has a portion that is pentagonal in cross-sections.

22. An instrument according to claim 12 wherein at least one of said strands has a portion that is hexagonal in cross-sections.

23. An instrument according to claim 12 wherein said at least one center strand is substantially straight with respect to at least one other strand.

24. An instrument according to claim 12 wherein said strands are bonded to each other at a body distal end.

25. An instrument according to claim 24 wherein said strands are bonded to each other at said body distal end by fusion.

26. An instrument according to claim 12 wherein at least some of said strands are twisted about each other.

* * * * *